US006211377B1

(12) United States Patent
de Schrijver et al.

(10) Patent No.: US 6,211,377 B1
(45) Date of Patent: Apr. 3, 2001

(54) PROCESS FOR THE PURIFICATION OF (±)-2-AZABICYCLO[2.2.1]HEPT-5-EN-3-ONE

(75) Inventors: Johny de Schrijver, Nieuwkerken; Philippe Otten, Lint, both of (BE)

(73) Assignee: Degussa-Huls AG, Frankfurt am Main (DE)

(*) Notice: Subject to any disclaimer, the term of this patent is extended or adjusted under 35 U.S.C. 154(b) by 0 days.

(21) Appl. No.: 09/260,142

(22) Filed: Mar. 1, 1999

(30) Foreign Application Priority Data

Feb. 27, 1998 (DE) .............................. 198 08 136

(51) Int. Cl.[7] .................................. C07D 221/02
(52) U.S. Cl. ........................ 546/183; 546/112; 548/512
(58) Field of Search ................... 546/112, 290, 546/183; 548/452, 512, 543, 552, 553

(56) References Cited

U.S. PATENT DOCUMENTS

| 5,200,527 | 4/1993 | Griffiths | 548/452 |
| 5,300,649 | 4/1994 | Griffiths | 546/290 |
| 5,847,157 | 12/1998 | Romanowski et al. | 548/512 |

FOREIGN PATENT DOCUMENTS

| 196 25 323 | 1/1998 | (DE) . |
| 0 508 352 | 10/1992 | (EP) . |
| 0 533 048 | 3/1993 | (EP) . |

OTHER PUBLICATIONS

Published Japanese Application 08027110A published on Jan. 30, 1996 (translation of abstract).

Chemical Abstracts, vol. 124, No. 23, 1996—Abstract 124: 316997a.

Primary Examiner—Sreeni Padmanabhan
(74) Attorney, Agent, or Firm—Pillsbury Madison & Sutro LLP

(57) ABSTRACT

A process for the purification of (±)-2-azabicyclo[2.2.1] hept-5-en-3-one wherein the purification is obtained exclusively by means of extraction procedures.

7 Claims, No Drawings

PROCESS FOR THE PURIFICATION OF (±)-2-AZABICYCLO[2.2.1]HEPT-5-EN-3-ONE

This application is based on Application No. 198 08 136.7 filed in Germany on Feb. 27, 1998, the content of which is incorporated here in by reference.

BACKGROUND OF THE INVENTION

1. Field of the Invention

The present invention relates to an improved process for the purification of (±)-2-azabicyclo[2.2.1]hept-5-en-3-one from its reaction solution.

2. Prior Art (±)-2-azabicyclo[2.2.1]hept-5-en-3-one is a starting material for the preparation of carbocyclic nucleoside analogues, which are of interest as therapeutic substances in medicine on account of their antiviral and chemotherapeutic properties.

The preparation of (±)-2-azabicyclo[2.2.1]hept-5-en-3-one is mentioned for example in EP 0 508 352, but the process described in said patent utilizes exclusively organic solvents to prepare the desired compound. The advantage of this process is the high purity with which the (±)-2-azabicyclo[2.2.1]hept-5-en-3-one can be recovered. The disadvantage, however, is the use of organic solvents in this reaction. Thus, advantageous modern processes all work with water as the reaction solvent.

The advantage of this modern variant is to be regarded as the fact that the entire synthesis can be carried out as a one-pot process starting from a suitable sulfinate, cyclopentadiene and cyanogen chloride. As one product of the reaction is the sulfinate used, this can successfully be recycled, making it possible substantially to reduce the operating costs of the process (EP 0 533 048 and DE 196 25 323).

In both the cases which have just been mentioned, the reaction solution advantageously prepared in this way is purified by extraction of the products into an organic solvent at pH values of approx. 8 in the aqueous phase.

The organic product phase is then concentrated and dried as described in EP 0 533 048 in order to isolate the product. The material obtained is orange or yellowish-brown in colour and has a content of <96% (HPLC).

According to DE 196 25 323, (±)-2-azabicyclo[2.2.1]hept-5-en-3-one can be crystallized from the organic phase after concentration. The losses of yield due to crystallization vary according to the position of the solubility equilibrium. Yields of light brownish-coloured product of <75% with contents of 98–99% (HPLC) are thus obtained by this purification strategy.

SUMMARY OF THE INVENTION

As described above, the (±)-2-azabicyclo[2.2.1]hept-5-en-3-one in question is an intermediate for the preparation of drugs. In view of the purity demands made on an authorized drug, the intermediate used to synthesize the active substance is therefore preferably one which is qualitatively particularly advantageous. A qualitatively advantageous intermediate is as colourless as possible and contains the lowest possible proportion of by-products.

At the same time, however, the intermediate should be economic to prepare, i.e. its purification must not require complicated and expensive procedures, and the yield of marketable material should be as high as possible.

One object of the present invention is therefore to develop a strategy for the purification of (±)-2-azabicyclo[2.2.1]hept-5-en-3-one prepared in aqueous solution, said strategy enabling the generation of a product which is as free as possible of by-products and as colourless as possible.

Another object consists in using this purification strategy to provide the product in yields comparable with the state of the art, as well as to improve its quality.

Another object is to design the purification procedure in such a way that it can be carried out with the minimum of complications and hence in an economically advantageous manner.

By extracting an aqueous reaction solution of (±)-2-azabicyclo[2.2.1]hept-5-en-3-one, originating from an aqueous preparative process, with an organic solvent, separating the phases and then re-extracting the product-containing organic solvent phase with water, an aqueous solution of (±)-2-azabicyclo[2.2.1]hept-5-en-3-one is obtained which contains 97% of the theoretically possible amount of product. Separation of the water and drying of the purified material gives a white powder with a purity of ≧99% (HPLC).

Completely surprisingly, but nevertheless advantageously, the purification process according to the invention yields a qualitatively superior material which was not known for this preparative process in the state of the art. The losses of yield with this purification strategy are so low that, despite the immense improvement in product quality, the yield is comparable to those of the state of the art.

(±)-2-azabicyclo[2.2.1]hept-5-en-3-one is very soluble in water. The purification described above yields an aqueous solution of the product purified according to the invention, which can be concentrated as desired and thus sold as a concentrated aqueous solution.

This is a very advantageous procedure because a technically complicated and economically disadvantageous crystallization and drying of the product can be dispensed with. This extremely surprising but nevertheless very advantageous effect is due to the good separation of the reaction by-products through the simple phase change of the product downstream of the organic extraction. This could in no way be predicted as crystallization is conventionally regarded as the optimum purification method for solids in terms of costs and purification effect.

Preferably, the extraction steps can be performed several times in succession, thereby minimizing the losses of yield. Extraction can optionally be carried out up to eight times in succession. Continuous extraction is also advantageous. To further reduce the loss of yield, it is advantageous to concentrate the organic product-containing phase, optionally under reduced pressure, before the second extraction with water. It is very particularly preferable to add sodium chloride to the aqueous product phase originating from the preparative process, before extraction with the organic solvent. Sodium chloride can optionally be added up to the saturation limit. The organic reaction products are thereby dissolved as completely as possible in the organic phase during extraction.

If desired, the (±)-2-azabicyclo[2.2.1]hept-5-en-3-one can be isolated from the final aqueous product phase by evaporation and drying.

Organic solvents which can be used for the primary extraction are any organic solvents which are immiscible with water, such as chlorinated hydrocarbons, ketones, ethers and the like. Preference is given to those which also have a low boiling point, as evaporation of the organic phase is otherwise made more difficult. Preferred solvents which can be used are methylene chloride, methyl tert-butyl ether, chloroform, methyl isobutyl ketone, methyl isopropyl ketone, nitromethane, nitroethane and 1- and 2-nitropropane.

It is particularly preferable to use MTBE.

The possibility of preparing a very pure aqueous solution of (±)-2-azabicyclo[2.2.1]hept-5-en-3-one is the reason why the product can be generated in a manner which is both economically and ecologically advantageous compared with the state of the art, since it avoids additional expensive purification steps and helps to save costs and energy.

DETAILED DESCRIPTION OF PREFERRED EMBODIMENTS OF THE INVENTION

The following Examples will illustrate the invention without however in any way limiting its scope.

Example 1

10 kg of dark brown aqueous reaction solution (containing 1.2 kg of (±)-2-azabicyclo[2.2.1]hept-5-en-3-one) are extracted with 30.7 kg of MTBE (8 extraction steps). The MTBE solution is evaporated to a 50% solution (1.2 kg of (±)-2-azabicyclo[2.2.1]hept-5-en-3-one in 1.2 kg of MTBE). 2.4 kg of water are added. The phases are stirred vigorously and then separated. The organic phase contains 2.5% of the (±)-2-azabicyclo[2.2.1]hept-5-en-3-one used. The aqueous phase is evaporated to a light yellow 60% solution of (±)-2-azabicyclo[2.2.1]hept-5-en-3-one.

Separation of the water and drying under reduced pressure gives 1.17 kg of off-white (±)-2-azabicyclo[2.2.1]hept-5-en-3-one (purity 99.3% (HPLC)), corresponding to a yield of 97%.

Example 2

580 g of dark brown aqueous reaction solution (containing 58 g of 2-azabicyclo[2.2.1]hept-5-en-3-one) are extracted with 3480 g of toluene (8 extraction steps). The toluene solution is evaporated to a 37.2% solution (30.5 g of 2-azabicyclo[2.2.1]hept-5-en-3-one in 51.5 g of toluene). 160 g of water are added. The phases are stirred vigorously and then separated. The organic phase contains 2.6% of the 2-azabicyclo[2.2.1]hept-5-en-3-one used. The aqueous phase is evaporated to a light yellow 60% solution of 2-azabicyclo[2.2.1]hept-5-en-3-one. Separation of the water and drying under reduced pressure gives 30.6 g of off-white 2-azabicyclo[2.2.1]hept-5-en-3-one (purity 99.6% (HPLC)), corresponding to a yield of 53%.

Example 3

573 g of dark brown aqueous reaction solution (containing 57.3 g of 2-azabicyclo[2.2.1]hept-5-en-3-one) are extracted with 6376 g of carbon tetrachloride (8 extraction steps). The carbon tetrachloride solution is evaporated to a 36.6% solution (20.6 g of 2-azabicyclo[2.2.1]hept-5-en-3-one in 35.7 g of carbon tetrachloride). 40 g of water are added. The phases are stirred vigorously and then separated. The organic phase contains 2.5% of the 2-azabicyclo[2.2.1]hept-5-en-3-one used. The aqueous phase is evaporated to a light yellow 60% solution of 2-azabicyclo[2.2.1]hept-5-en-3-one. Separation of the water and drying under reduced pressure gives 19.1 g of off-white 2-azabicyclo[2.2.1]hept-5-en-3-one (purity 99.1% (HPLC)), corresponding to a yield of 33%.

Comparative Example 10 kg of dark brown aqueous reaction solution (containing 1.2 kg of (±)-2-azabicyclo[2.2.1]hept-5-en-3-one) are extracted with 30.7 kg of MTBE (8 extraction steps). The MTBE solution is evaporated to a 25% solution (1.2 kg of (±)-2-azabicyclo[2.2.1]hept-5-en-3-one in 3.6 kg of MTBE). Freezing-out and drying under reduced pressure gives 0.9 kg of light brown-coloured (±)-2-azabicyclo[2.2.1]hept-5-en-3-one (purity 98.4% (HPLC)), corresponding to a yield of 74%.

What is claimed is:

1. A process for the purification of an aqueous reaction solution of (±)-2-azabicyclo{2.2.1}hept-5-en-3-one obtained from an aqueous preparative process, comprising:

extracting the aqueous reaction solution with an organic solvent;

separating a resulting organic phase containing the (±)-2-azabicyclo{2.2.1}hept-5-en-3-one from a resulting aqueous phase;

mixing the resulting organic phase with water; and separating the resulting phases.

2. A process according to claim 1, wherein the individual extraction steps are carried out up to eight times in succession.

3. A process according to claim 1, wherein the organic phase is concentrated, optionally under reduced pressure, before the second extraction.

4. A process according to claim 1, wherein sodium chloride is added to the aqueous phase before the first extraction.

5. A process according to claim 1, wherein the (±)-2-azabicyclo[2.2.1]hept-5-en-3-one is isolated from the final aqueous product phase by evaporation.

6. A process according to claim 1, wherein the organic solvent used is methylene chloride, methyl tert-butyl ether, chloroform, methyl isobutyl ketone, methyl isopropyl ketone, nitromethane, nitroethane or 1- or 2-nitropropane.

7. A process according to claim 1, wherein MTBE is used as the organic solvent.

* * * * *